(12) United States Patent
Bassin

(10) Patent No.: US 11,951,255 B2
(45) Date of Patent: *Apr. 9, 2024

(54) METHODS AND APPARATUS WITH IMPROVED VENTILATORY SUPPORT CYCLING

(71) Applicant: ResMed Pty Ltd, Bella Vista (AU)

(72) Inventor: David John Bassin, Coogee (AU)

(73) Assignee: ResMed Pty Ltd (AU)

( * ) Notice: Subject to any disclaimer, the term of this patent is extended or adjusted under 35 U.S.C. 154(b) by 936 days.

This patent is subject to a terminal disclaimer.

(21) Appl. No.: 16/947,078

(22) Filed: Jul. 17, 2020

(65) Prior Publication Data

US 2021/0008311 A1 Jan. 14, 2021

Related U.S. Application Data

(63) Continuation of application No. 15/294,248, filed on Oct. 14, 2016, now Pat. No. 10,751,491, which is a
(Continued)

(51) Int. Cl.
*A61M 16/00* (2006.01)
*A61M 16/06* (2006.01)

(52) U.S. Cl.
CPC .... *A61M 16/0069* (2014.02); *A61M 16/0003* (2014.02); *A61M 16/0051* (2013.01);
(Continued)

(58) Field of Classification Search
CPC .... A61M 16/00–0003; A61M 16/0051; A61M 16/0057–0069;
(Continued)

(56) References Cited

U.S. PATENT DOCUMENTS

| 4,449,537 A | 5/1984 | Pross et al. |
| 5,303,700 A | 4/1994 | Weismann et al. |

(Continued)

FOREIGN PATENT DOCUMENTS

| EP | 1205202 A2 | 5/2002 |
| JP | 2002159577 A | 6/2002 |
| WO | 2002028460 A1 | 4/2002 |

OTHER PUBLICATIONS

Extended European Search Report for Application No. 14170926.1 dated Aug. 6, 2014.
(Continued)

*Primary Examiner* — Rachel T Sippel
(74) *Attorney, Agent, or Firm* — Botos Churchill IP Law LLP

(57) ABSTRACT

A ventilator that delivers air at different pressures to a patient during inspiratory and expiratory cycles of breathing and that cycles from inspiratory to expiratory operation when the patient's respiratory flow passes a threshold level. The threshold generally increases from the beginning of inspiration to the end of inspiration. The increase can be linear over all or only a portion of the inspiratory cycle, and the threshold can be adjusted so that cycling is prevented during the initial portion of an inspiratory cycle. The minimum and maximum levels may both be functions of peak flow and the threshold may increase as a function of elapsed inspiratory time. The rate at which the threshold increases from a minimum level to a maximum level may be adjustable for individual patient needs and may be determined from previous breaths.

18 Claims, 7 Drawing Sheets

Related U.S. Application Data continuation of application No. 14/448,093, filed on Jul. 31, 2014, now Pat. No. 9,504,795, which is a continuation of application No. 11/571,068, filed as application No. PCT/AU2005/000895 on Jun. 22, 2005, now Pat. No. 8,826,906.

(60) Provisional application No. 60/582,580, filed on Jun. 23, 2004.

(52) U.S. Cl.
CPC ..... *A61M 16/06* (2013.01); *A61M 2016/0015* (2013.01); *A61M 2016/0018* (2013.01); *A61M 2016/0021* (2013.01); *A61M 2016/0027* (2013.01); *A61M 2016/003* (2013.01); *A61M 2016/0036* (2013.01); *A61M 2016/0039* (2013.01); *A61M 2205/3303* (2013.01); *A61M 2205/50* (2013.01)

(58) Field of Classification Search
CPC . A61M 16/021–024; A61M 2016/0015–0018; A61M 2016/0027–0042
See application file for complete search history.

(56) References Cited

U.S. PATENT DOCUMENTS

| | | |
|---|---|---|
| 5,551,419 A | 9/1996 | Froehlich et al. |
| 5,647,351 A | 7/1997 | Weismann et al. |
| 5,740,795 A | 4/1998 | Brydon |
| 6,237,593 B1 | 5/2001 | Brydon |
| 6,318,365 B1 | 11/2001 | Voegele et al. |
| 6,332,463 B1 | 12/2001 | Farrugia et al. |
| 6,439,229 B1 | 8/2002 | Du et al. |
| 6,626,176 B1 | 9/2003 | Madaus et al. |
| 9,504,795 B2 | 11/2016 | Bassin |

OTHER PUBLICATIONS

International Search Report and Written Opinion for PCT/AU2005/000895 dated Aug. 31, 2005.
Japanese Patent Office, Notice of Reasons of Rejection, Application No. P2007-516889, Dispatch No. 123553, Dispatch Date: Feb. 22, 2011.
Non-Final Office Action dated May 16, 2019.

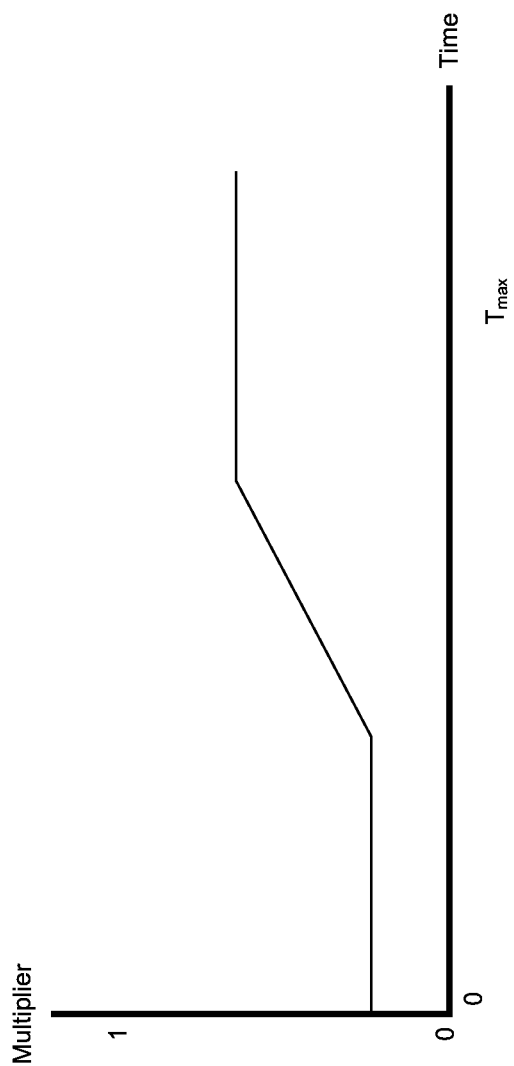

METHODS AND APPARATUS WITH IMPROVED VENTILATORY SUPPORT CYCLING

CROSS-REFERENCE TO RELATED APPLICATIONS

The present application is a continuation of U.S. patent application Ser. No. 15/294,248 filed Oct. 14, 2016, which is a continuation of U.S. patent application Ser. No. 14/448,093 filed Jul. 31, 2014, now U.S. Pat. No. 9,504,795, which is a continuation of U.S. patent application Ser. No. 11/571,068 filed Dec. 21, 2006, now U.S. Pat. No. 8,826,906, which is a national phase entry under 35 U.S.C. § 371 of International Application No. PCT/AU2005/000895 filed Jun. 22, 2005, published in English, which claims priority from U.S. Provisional Patent Application No. 60/582,580 filed Jun. 23, 2004, all of which are incorporated herein by reference.

TECHNICAL FIELD

The invention relates to methods and apparatus for the provision of ventilatory assistance synchronized with a subject's respiratory cycle. More specifically, the invention relates to methods for synchronizing the ventilator to cycle its pressure response in conjunction with the patient's respiration cycle.

BACKGROUND

The present invention is applicable to any form of ventilation in which respiratory flow is used for cycling, although it is primarily useful in noninvasive pressure-support ventilation. The invention also finds use in invasive ventilation, especially of the pressure support variety. The invention finds greatest use in the presence of higher levels of pressure support, with patients who typically do not have sleep apnea but do have respiratory insufficiency or failure, where ventilatory assistance is typically provided mainly at night but may well be provided during some of the daytime. Cycling becomes a prominent issue when respiratory mechanics are abnormal, especially in chronic obstructive pulmonary disease (COPD).

In a ventilator, it is often necessary to have a control process to detect when the patient's actual respiratory cycle switches from inspiration to expiration or vice versa so that the ventilatory can implement an appropriate ventilation response. For example, some ventilatory devices provide a process for determining when to trigger an inspiratory pressure for purposes of delivering an appropriate pressure during the inspiratory portion of the patient's respiratory cycle. Similarly, such a device may also have a process for determining when to cycle to an expiratory pressure for purposes of delivery of an appropriate machine-patient response during the patient's expiration. Such processes serve to synchronize the ventilator with the patient's actual respiratory cycle. Those skilled in the art will recognize that "triggering" is the event associated with the initiation of the pressure levels intended for the patients inspiration and "cycling" is the event associated with switching to the pressure levels intended for the patient's expiration.

For example, a bi-level ventilator provides a higher pressure level during the inspiratory portion of the patient's breathing cycle, a so-called IPAP, and a lower pressure level during the expiratory portion of the breathing cycle, a so-called EPAP. Traditionally, the switching may be accomplished by monitoring the respiratory flow or pressure and defining a threshold level, such as zero or a percentage of peak flow. When the measured respiratory flow value falls below the threshold, the device will deliver the EPAP. Another alternative to such switching may involve recorded respiration rates and the monitoring of elapsed time from the start of inspiration; the machine may switch to the expiratory portion of the respiratory cycle after reaching a time that is the expected time for the inspiratory portion of the respiratory cycle.

A goal of these processes for cycling is to make a ventilator device more comfortable for a user because if respiratory events are not properly synchronized, the device may be quite uncomfortable for a patient. A considerably more important goal is to optimize gas exchange and, especially in COPD with severe expiratory flow limitation, to prevent prolonged inspiratory times which lead to dynamic hyperinflation. Current methods for cycling can sometimes improperly detect expiration and result in an improper pressure change. For example, if the ventilator cycles into expiration too early, less support will be provided to the patient during inspiration when it is needed. Thus, there is need to improve such processes by minimizing improper synchronization.

BRIEF SUMMARY

It is an objective of the invention to improve synchronization by providing a variable cycling threshold that changes as a function of time.

It is a further objective of the invention to provide a synchronization expiratory threshold that changes to become more sensitive during inspiration as the cycle advances.

Additional objectives will be apparent to those skilled in the art upon consideration of the following description of the invention.

In the invention, a synchronization threshold is calculated that is compared to a measure of flow for purposes of determining whether the ventilator should advance from inspiration to expiration. In a preferred embodiment, the threshold is a function of time that permits it to change within a single inspiratory cycle from a less sensitive threshold during early portions of the cycle to a more sensitive threshold during latter portions of the cycle. In one embodiment of the invention, the threshold is provided with a refractory period to prevent a transition to expiration during certain times within a cycle when such a transition is not desired or unlikely to accurately reflect the patient's actual advance to expiration. Additional aspects of the invention are described in more detail in the following specification.

BRIEF DESCRIPTION OF THE DRAWINGS

FIG. 2B is a graph of a sensitivity function for varying an expiratory synchronization threshold with time within a cycle;

DETAILED DESCRIPTION

Figure 1:
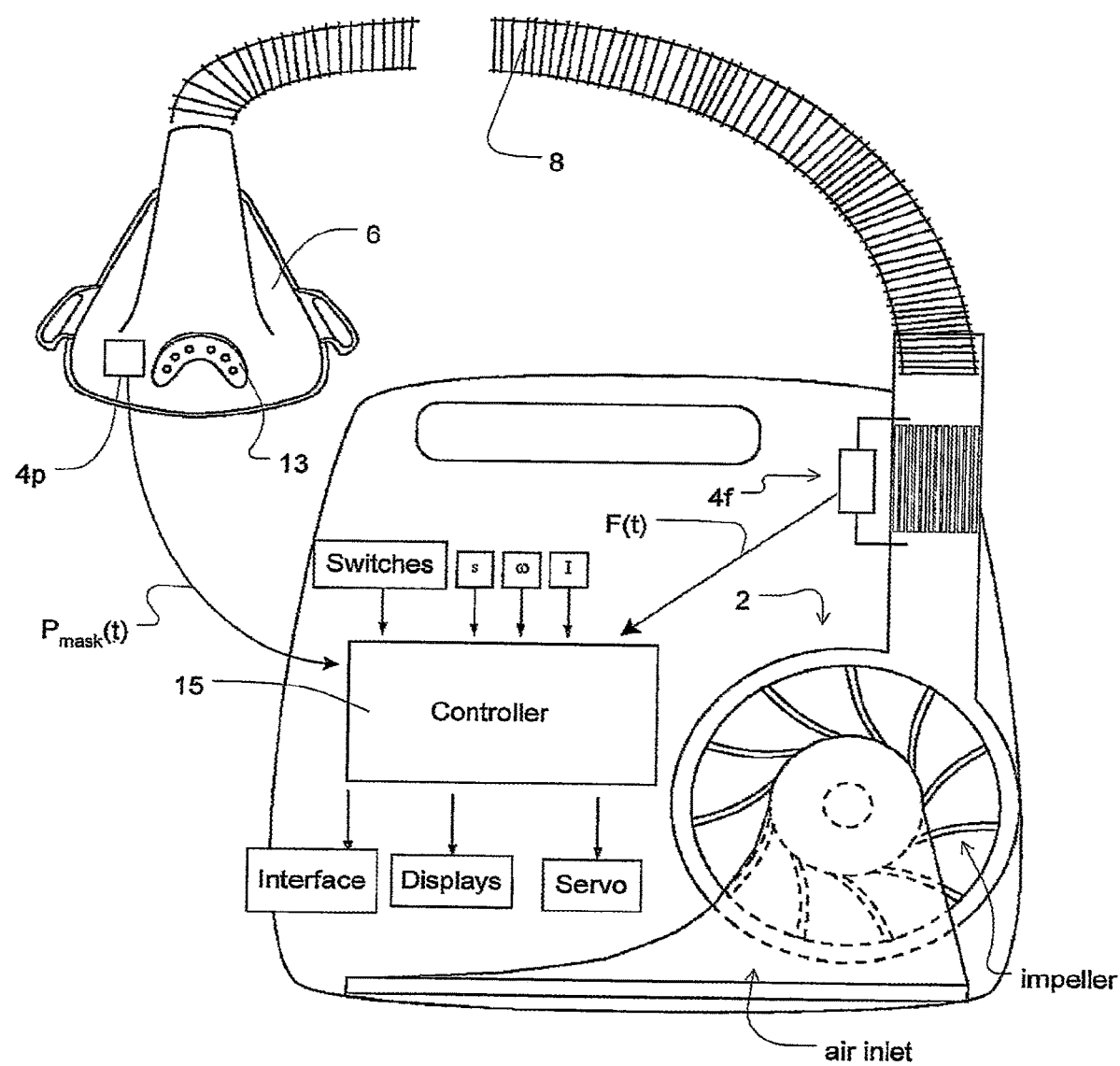
FIG. 1 depicts the structure of the preferred ventilator apparatus for implementing the methods of the current invention.

In reference to FIG. 1, the pressure delivery device includes a servo-controlled blower 2, a mask 6, and an air delivery conduit 8 for connection between the blower 2 and the mask 6. Exhaust gas is vented via exhaust 13. Optionally, a flow sensor 4f and/or pressure sensor 4p may also be utilized in which case mask flow may be measured using a pneumotachograph and differential pressure transducer or similar device to derive a flow signal F(t), and mask pressure is measured at a pressure tap using a pressure transducer to derive a pressure signal $P_{mask}(t)$. The pressure sensor 4f and flow sensor 4p have only been shown symbolically in FIG. 1 since it is understood that those skilled in the art would understand how to measure flow and pressure. Flow F(t) and pressure $P_{mask}(t)$ signals are sent to a controller or microprocessor 15 to derive a pressure request signal $P_{request}(t)$. P Alternatively, a flow signal f(t) and pressure signal $P_{mask}(t)$ may be estimated or calculated in relation to the blower motor by monitoring current supplied to the motor and/or the speed of the motor as disclosed in U.S. Pat. Nos. 5,740,795, 6,332,463 or 6,237,593 without the provision of flow and pressure sensors as described above. Optionally, the blower motor speed may be held generally constant and pressure changes in the mask may be implemented by controlling an opening of a servo-valve that may variably divert or deliver airflow to the mask.

A controller 15 or processor is configured and adapted to implement the methodology described in more detail herein and may include integrated chips, a memory and/or other instruction or data storage medium. For example, programmed instructions with the control methodology may be coded on integrated chips in the memory of the device or loaded as software.

Preferably, the device delivers varying pressure levels of continuous positive airway pressure which are generally higher during inspiration than expiration. However, consistent with the control principles of the invention as described herein, other types of ventilatory pressure treatment may be implemented in the apparatus, such as other more comfortable variants of natural patient-synchronized pressure changes.

In accordance with the principles of my invention, the synchronization threshold is varied within a single inspiratory breathing cycle as a function of time. In other words, the threshold does not remain constant during the cycle. Rather, the threshold increases over time to make it more sensitive during the inspiratory cycle and thus render the threshold more likely to result in the cycling of the ventilator as the inspiratory cycle advances to expiration. For example, a variable cycling threshold may be continuously calculated by the device as the inspiratory time lapses and it can be changed during that time period until expiration is detected by the flow falling below the threshold. Another way of looking at the invention is that the ventilator becomes increasingly sensitive to the initiation of cycling as inspiration progresses.

Figure 2:
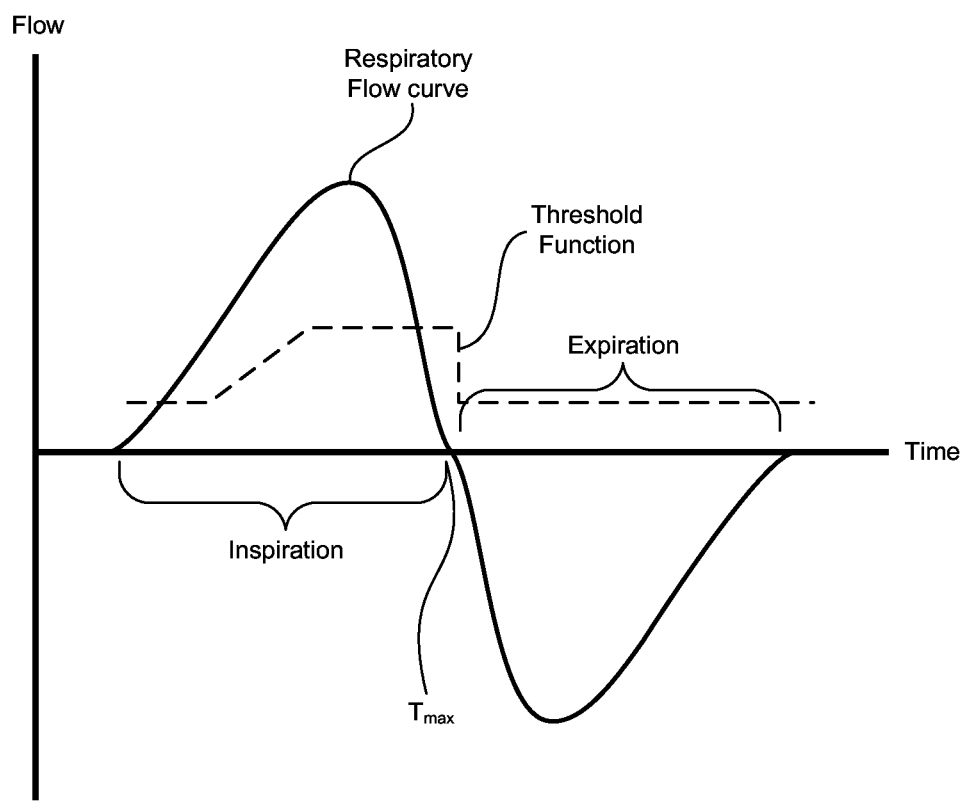
FIG. 2. is a graph of one embodiment of an expiratory synchronization threshold that varies with time within a cycle.

One example of this invention is illustrated in FIG. 2. In the figure, the cycling threshold function (shown as a dashed line) for detecting expiration is changed during the course of inspiration from less sensitive to more sensitive. This increase in sensitivity improves synchronization because with such an in-cycle varying threshold, the device is less likely to inadvertently switch into expiration in an early stage of inspiration but, as inspiration advances, the threshold becomes more likely to cause the ventilator to switch into expiration. In other words, it is more difficult to cycle during the early parts of inspiration and easier during the latter portions of inspiration.

In the embodiment, the threshold varies as a function of time, $T_{max}$, which preferably is the expected time of the inspiration. Moreover, the threshold may optionally be restricted to vary between a minimum threshold value and/or a maximum threshold value. In one embodiment, the maximum and minimum thresholds may be a function of peak flow, such as a proportion or percentage of a previous breath's peak flow, e.g., 50% and 10% respectively. Alternatively, the maximum and minimum thresholds may be some predefined fixed amount above a zero based flow measure. A clinician or physician may select these percentages or amounts.

Between the minimum and maximum, the threshold is preferably an increasing function such as an increasing function of elapsed inspiratory time. For example, the increasing function may be a ratio of elapsed inspiratory time ($T_{insp\_elapsed}$) to expected inspiratory time $T_{max}$(e.g., $k*T_{insp\_elapsed}/T_{max}$), where k is a preset sensitivity constant that can be adjusted higher for patients that need a faster increase in sensitivity to permit quicker cycling to expiration for patients that need faster cycling. In one embodiment, the $T_{max}$ or expected inspiratory time is determined from previous breaths, for example, as the average inspiration time from the previous five normal breaths (excluding coughs etc.). Alternatively, $T_{max}$ may be a preset maximum inspiration cycle time. The elapsed inspiration time $T_{insp\_elapsed}$ counter can be set to 0 during expiration and begin counting at the beginning of inspiration. For example, the threshold may be set as follows:

Temp_Threshold=$(k*T_{insp\_elapsed}/T_{max})$*max_threshold
If Temp_threshold<min_threshold then
Set Threshold to the min_threshold
Else if Temp_threshold>max_threshold then
   Set Threshold to max_threshold
Else
   Set Threshold to the temp_threshold
Other alternative schemes may be utilized for varying the cycling threshold as a function of inspiratory time. For example, the synchronization threshold may be set (a) to the minimum threshold during a first portion of the expected inspiratory period, e.g., about 25% of the expected cycle time, (b) to ramp from the minimum threshold to the maximum threshold during a middle portion of the expected inspiratory period, (e.g., about the next 50% of the expected inspiratory cycle time), and (c) to the maximum threshold for the last portion of the expected inspiratory period (e.g., about the last 25% of the expected cycle time). Such a function may be implemented by a threshold multiplier or threshold sensitivity function as illustrated by the graph of FIG. 2B. Utilizing the function of FIG. 2B, a synchronization threshold for cycling may be calculated by the following formula:

$$\text{Threshold}=Ts(t)*\text{Peak\_Flow}$$

where:
Ts(t) is a threshold sensitivity function of inspiratory cycle time that results in a multiplier between 0 and 1 as illustrated by the graph in FIG. 2B; and
Peak_Flow is the peak inspiratory flow.

In the illustrated graph of FIG. 2B, during the first portion of the inspiratory cycle, the multiplier may be 0 or a low value (e.g., 0.10), and as the cycle advances the multiplier can ramp to a maximum level (e.g., 0.60). Those skilled in the art will recognize different forms of the multiplier graph that can be produced for the threshold sensitivity function for increasing the sensitivity of the threshold over time within a cycle to implement effective cycling thresholds. In all embodiments of my invention, the threshold generally increases from the beginning of inspiration to the end of inspiration. In one form the rate of increase is constant.

Figure 3:
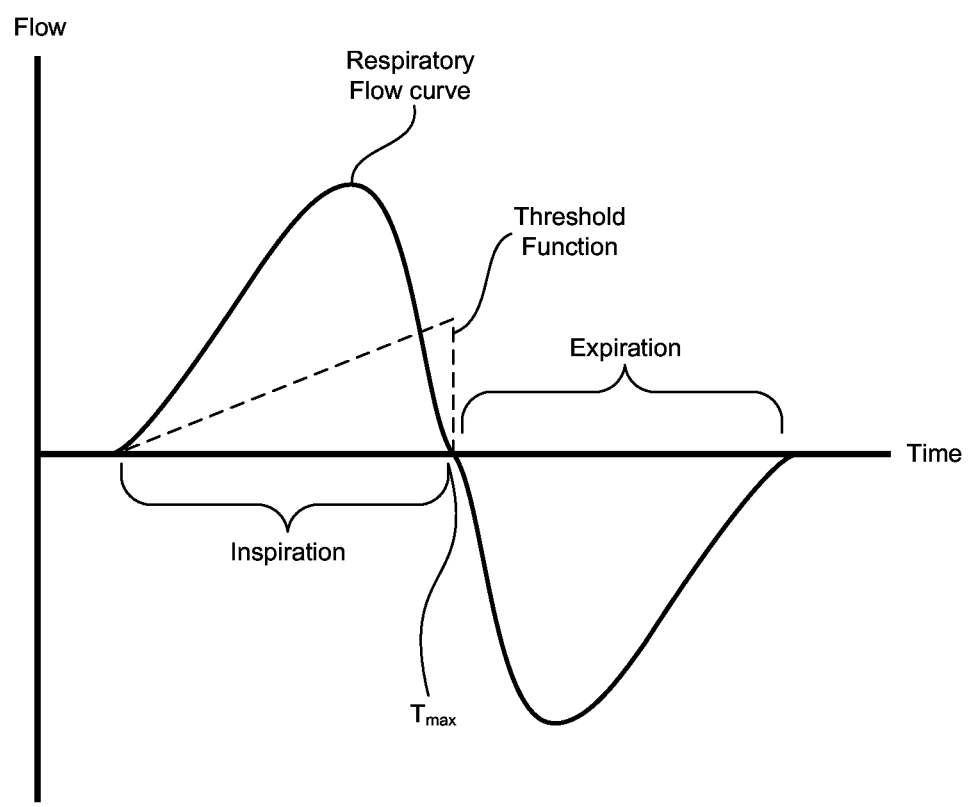
FIG. 3 is a graph of another embodiment of an expiratory synchronization threshold that varies with time within a cycle.

In another embodiment, as illustrated in FIG. 3, the threshold may ramp as a monotonically increasing function. The ramp may start at 0 flow at the beginning of inspiration and increase as the inspiratory portion of the respiratory cycle advances.

This embodiment may be implemented by the formula described with regard to the embodiment of FIG. 2 by setting the minimum threshold to 0 and the sensitivity constant to 1. The maximum threshold may be set to some desired percentage of peak flow. In this way, as the time of the patient's inspiration approaches the expected time or some predetermined maximum time, the cycling threshold will gradually ramp up to the preset maximum percentage of peak flow. Alternatively, with regard to the sensitivity function of FIG. 2B, the graph of the multiplier may start at 0 and increase to a higher level. It is clear that in the case of timed breaths, since the flow is typically zero or negative at the start of a timed breath, this algorithm will cause immediate cycling, since the actual flow is less that the cycling threshold of 0. Hence this cycling threshold function is applicable as stated only with triggered breaths, but may be used in combination with an absolute refractory period (minimum inspiratory time before cycling can occur) which allows time for the pressure support delivered by the ventilator to cause the flow to be significantly positive by the end of the absolute refractory period. (Alternatively, cycling can be controlled to take place when the flow crosses the threshold only in the downward direction.)

Figure 4:
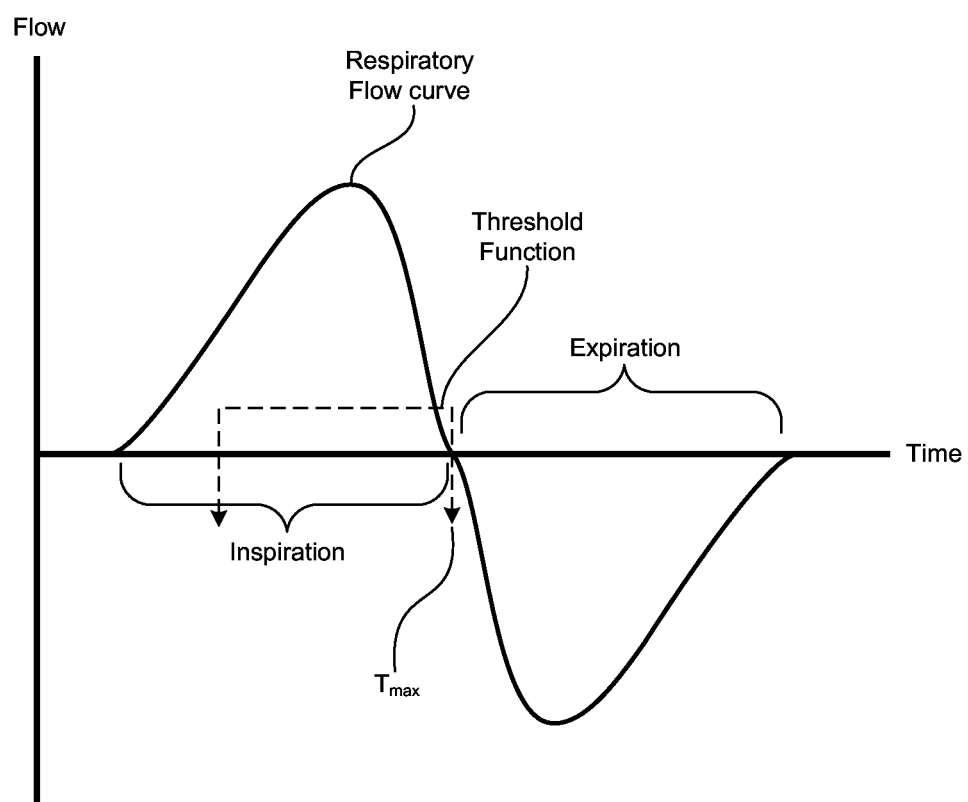
FIG. 4 is a graph of one embodiment of an expiratory synchronization threshold that includes a refractory period within a cycle.

In one embodiment, a refractory period is implemented to prevent cycling to expiration during a certain time period. For example, such an implementation is illustrated in the graph of FIG. 4. In FIG. 4, a constant threshold is illustrated with a refractory period that is a function of inspiratory time. In the illustrated example, the cycling threshold is inoperable at the beginning of inspiration, thus preventing cycling during the refractory period. Although the cycling threshold can be at a desired percentage of a peak flow that will cycle the ventilator properly, during the refractory period it may be set to a level that will prevent cycling, (e.g., −4*peak flow). However, after the lapsing of the refractory period, the threshold steps up to return to the desired operable threshold level. For example, the threshold may be set to be inoperable during the first 25% of the expected time for the inspiratory cycle ($T_{max}$) as follows:

If ($T_{insp\_elapsed}$<0.25*$T_{max}$) then

Threshold=−4*peak flow

Else

Threshold=0.25*peak flow.

Figure 5:
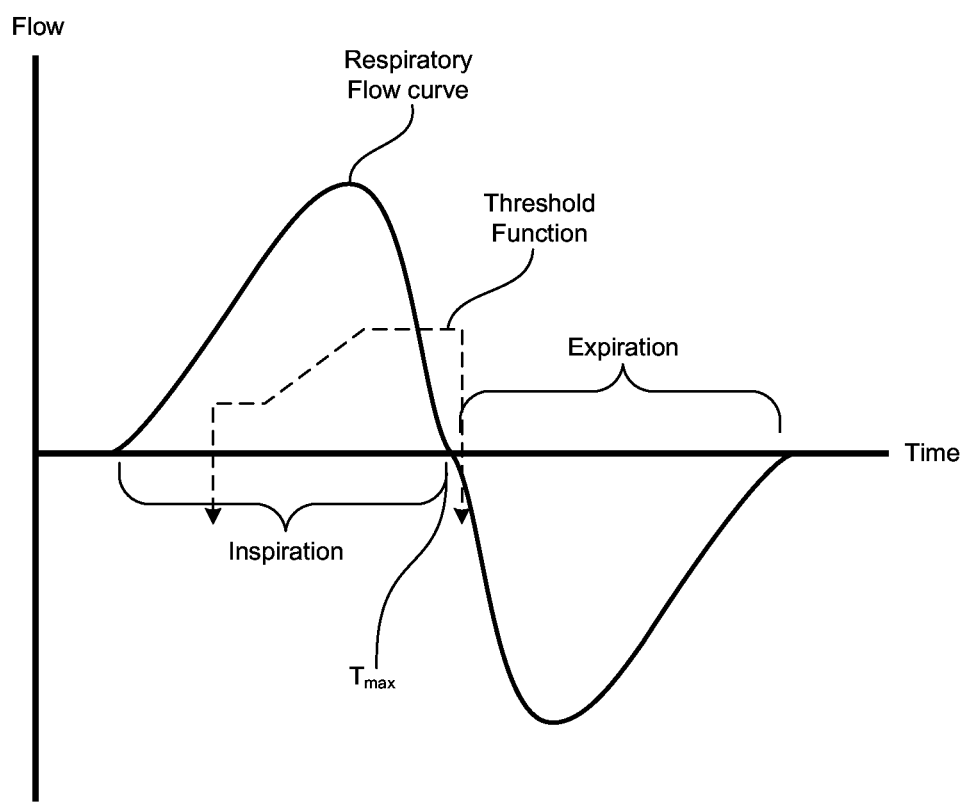
FIG. 5 is a graph of one embodiment of an expiratory synchronization threshold that varies with time within a cycle and includes a refractory period.

Similarly, such a refractory period may be implemented for the increasing functions of the earlier embodiments disclosed in FIGS. 3 and 4. For example, as illustrated by the cycling threshold of FIG. 5, the increasing function that is restricted between minimum and maximum thresholds has a refractory period during an early portion of inspiration and only becomes effective thereafter.

Figure 6:
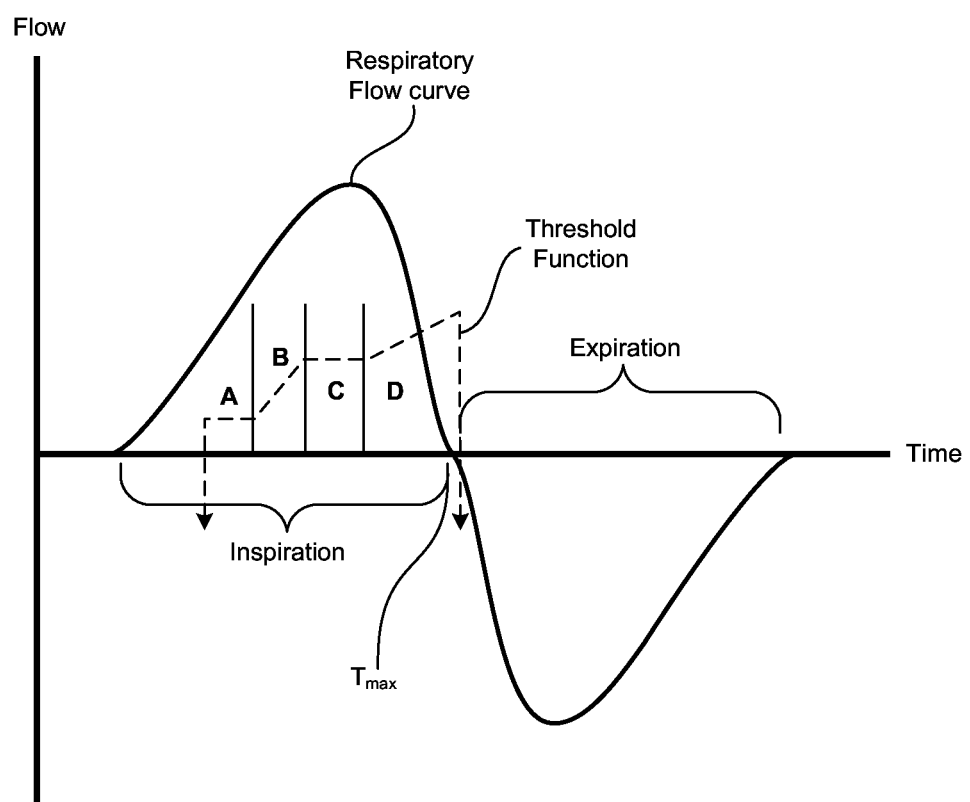
FIG. 6 is a graph of another embodiment of an expiratory synchronization threshold that varies with time within a cycle.

Various aspects of the previously described implementations may be combined to create other dynamic thresholds for synchronizing a ventilator. One such combination is illustrated in FIG. 6. In the graph, during a first time portion of the cycle, a refractory period is enforced. In the next time portion of the cycle (A), a minimum threshold is applied. In the following time portion (B), the threshold is ramped from the minimum threshold to a second tier threshold. The second tier threshold is applied during a fourth time period (C). Finally, in the final period D, the threshold is an increasing function of a maximum from the second tier threshold.

The respiratory mechanics of timed and triggered breaths differ. In a timed breath, the respiratory flow may be significantly negative at the start of the breath, and patient effort may occur only sometime after the start of the breath or not at all. With a low pressure support level, early cycling may occur, particularly if the cycling threshold is a fixed value or is the maximum of a proportion of peak flow and some fixed minimum (positive) cycling threshold. In the case of a pressure support servoventilator, in which the pressure support level may be quite low during a period of spontaneous breathing, the consequence may be that the first one or two breaths after a transition from triggered to timed breaths may be relatively ineffective, and certainly less effective than if premature cycling had not occurred. For this and other reasons there is an advantage in having different cycling threshold algorithms for timed and triggered breaths.

Under some circumstances, typically during a timed breath, there is an advantage in having a moderately negative cycling threshold for some proportion of inspiration. This means that the inspiration can be terminated by a patient effort, but will not be terminated passively. At the end of the period of negative cycling threshold, the cycling threshold may change abruptly or smoothly towards a more positive value.

Cycling threshold during part or all of the inspiratory time may be a function both of some predetermined constant values and some function of respiratory flow, such as (instantaneous) peak respiratory flow.

In a preferred embodiment a number of these features are combined so that the cycling algorithm during a timed breath is as follows:

There is a maximum inspiratory time TiMax, at which cycling will occur regardless of any other conditions. TiMax is set to a value that is reasonable for timed breaths; for example, if the timed respiratory period (the reciprocal of the backup rate) is TTotTimed, TiMax is equal to a reasonable inspiratory fraction for the patient in question (typically between 0.25 and 0.4) multiplied by TTotTimed.

For inspiratory time in (0, TiMax/6) cycling cannot occur.
For inspiratory time in (TiMax/6, TiMax/3) the cycling threshold is some small negative value, QCycMin, such as −0.1 l/s.
Let QPeak(Ti) denote instantaneous peak flow at inspiratory time Ti.
Let QPeaksPos (Ti)=max (instantaneous peak flow QPeak (Ti), 0)
For inspiratory time Ti in (TiMax/3, TiMax*2/3) the cycling threshold QCyc is given by interpolation between the value QCycMin at the start of this inspiratory time interval and a threshold equal to a proportion FCyc of QPeakPos (Ti) at the end of this inspiratory time interval, in particular by:

QCyc=(Ti−TiMax/3)/(TiMax*2/3−TiMax/3)*(FCyc*QPeakPos(Ti)−QCycMin)+QCycMin

For inspiratory time Ti in (TiMax*2/3, TiMax) the cycling threshold QCyc is given by a proportion FCyc of QPeakPos (Ti).

Although the invention has been described with reference to various embodiments as described in this entire disclosure, it is to be understood that these embodiments are merely illustrative of an application of the various principles of the invention. Numerous modifications, in addition to the illustrative embodiments of the invention discussed herein may be made and other arrangements may be devised without departing from the spirit and scope of the invention. For example, although cycling thresholds have generally been graphically illustrated in this disclosure, analogous thresholds may be implemented as triggering thresholds for inspiration.

The invention claimed is:

1. An apparatus that controls changes to delivery of ventilation in relation to inspiratory and expiratory cycles of a patient's breathing, the apparatus comprising:
   a controller comprising a processor and configured to:
   receive data indicative of respiratory flow, the data including inspiratory cycle data for an inspiratory cycle, and
   determine a computed threshold flow level by computing a threshold flow level that varies as a function of elapsed inspiratory time and that is a predetermined amount above a zero level for at least a portion of a respiratory cycle,
   wherein the controller is configured to control cycling from an inspiratory operation to an expiratory operation based on a comparison of the inspiratory cycle data to the computed threshold flow level.

2. The apparatus according to claim 1 wherein the apparatus comprises a motor operated gas source for producing ventilation flow for the patient's breathing.

3. The apparatus according to claim 2 wherein the apparatus comprises a servo-valve and wherein the controller is configured to control operation of the servo-valve for controlling the changes to delivered ventilation.

4. The apparatus according to claim 2 wherein the motor operated gas source is a blower and wherein the controller is configured to control changes in speed of the blower for controlling the changes to delivered ventilation.

5. The apparatus according to claim 2, wherein the controller is further configured to compare the inspiratory cycle data to the computed threshold flow level and control the apparatus to cycle from the inspiratory operation to the expiratory operation.

6. The apparatus according to claim 2, wherein the computed threshold flow level increases from a minimum level to a maximum level during the inspiratory cycle.

7. The apparatus according to claim 6, wherein the controller is configured to compute the minimum and maximum levels as a function of a multiplier and peak inspiratory flow data included in the received data indicative of respiratory flow.

8. The apparatus according to 2, wherein the computed threshold flow level increases from a minimum level to a maximum level as a function of elapsed inspiratory time and a predetermined maximum inspiratory time.

9. The apparatus according to claim 2, wherein the controller is configured to cause the apparatus to cycle from the inspiratory operation to the expiratory operation by controlling a motor current.

10. The apparatus according to claim 2, further comprising a flow sensor for deriving the data indicative of respiratory flow associated with the patient's breathing.

11. The apparatus according to claim 2, further comprising a pressure sensor for deriving airway pressure data and providing the airway pressure data to the controller.

12. A method for controlling a ventilation apparatus to change between an inspiratory operation and an expiratory operation, the method comprising:
    detecting data indicative of respiratory flow for an inspiratory cycle;
    determining a computed threshold flow level by computing a threshold flow level that varies as function of elapsed inspiratory time of a respiratory cycle and that is a predetermined amount above a zero level for at least a portion of the respiratory cycle;
    comparing the computed threshold flow level to the detected data indicative of respiratory flow; and
    changing the ventilation apparatus from the inspiratory operation to the expiratory operation based on the comparing.

13. The method according to claim 12, wherein the computed threshold flow level varies from a minimum value to a maximum value.

14. The method according to claim 12, wherein the computed threshold flow level is set to prevent cycling to expiration during a certain time period.

15. The method according to claim 12, wherein the computed threshold flow level increases from a minimum level to a maximum level as a function of the elapsed inspiratory time and a predetermined maximum inspiratory time.

16. The method according to claim 15 wherein the ventilation apparatus comprises a motor operated gas source for producing ventilation flow for a patient's breathing.

17. The method according to claim 16 wherein the ventilation apparatus comprises a servo-valve and wherein the servo-valve is controlled for changing the produced ventilation flow.

18. The method according to claim 16 wherein the motor operated gas source is a blower and wherein the speed of the blower is controlled for changing the produced ventilation flow.

* * * * *